(12) United States Patent
Grieshaber et al.

(10) Patent No.: US 6,561,974 B1
(45) Date of Patent: May 13, 2003

(54) DEVICE FOR USE IN A SURGICAL PROCEDURE ON AN EYE OF A LIVING BEING, AND METHOD OF RETRACTING THE IRIS

(75) Inventors: Hans R. Grieshaber, Schaffhausen (CH); Werner Maag, Glarus (CH); Gerhard Althoff, Winkel/Bülach (CH)

(73) Assignee: Grieshaber & Co. AG Schaffhausen, Schaffhausen (CH)

( * ) Notice: Subject to any disclaimer, the term of this patent is extended or adjusted under 35 U.S.C. 154(b) by 0 days.

(21) Appl. No.: 09/583,517

(22) Filed: May 31, 2000

(51) Int. Cl.$^7$ .................................................. A61B 1/32
(52) U.S. Cl. ........................ 600/206; 600/209; 600/217; 600/236
(58) Field of Search ................................. 600/201, 206, 600/209, 210, 217, 235, 236

(56) References Cited

U.S. PATENT DOCUMENTS

| | | | | |
|---|---|---|---|---|
| 4,955,889 A | * | 9/1990 | Van Gent | 606/107 |
| 4,959,067 A | * | 9/1990 | Muller | 606/109 |
| 4,991,567 A | * | 2/1991 | McCuen, II et al. | |
| 5,174,279 A | * | 12/1992 | Cobo et al. | |
| 5,192,301 A | | 3/1993 | Kamiya et al. | |
| 5,370,109 A | * | 12/1994 | Cuny | 606/798 |
| 5,450,842 A | * | 9/1995 | Tovey et al. | 600/206 |
| 5,514,076 A | * | 5/1996 | Ley | 600/206 |
| 5,556,417 A | | 9/1996 | Sher | |
| 5,716,328 A | | 2/1998 | Grieshaber et al. | |
| 5,807,244 A | * | 9/1998 | Barot | 600/236 |
| 5,871,496 A | | 2/1999 | Ginn et al. | |

FOREIGN PATENT DOCUMENTS

| | | |
|---|---|---|
| DE | 43 01 418 A | 3/1995 |
| EP | 0 653 197 A1 | 5/1995 |
| WO | WO-99/37215 A1 * | 7/1999 |

OTHER PUBLICATIONS

Cornetto Ad et al.: "Reusable superlastic iris retractor" Ophtalmic Surgery and Lasers, Bd. 30, No. 7, Jul. 1999 pp. 586–587, XP001025579 * the entire document *.

* cited by examiner

Primary Examiner—Jeffrey A. Smith
(74) Attorney, Agent, or Firm—Henry M. Feiereisen

(57) ABSTRACT

A device for use in a surgical procedure on an eye of a living being, includes a retraction member, destined for insertion into the anterior chamber of the eye. The retraction member has a hook-shaped engagement part for retracting the iris, whereby at least the engagement part of the retraction member is made of a deformable material with shape memory. Thus, the retraction member is insertable into the anterior chamber with the engagement part exhibiting a substantially straight configuration, and subsequently the engagement part is able to recover its original hook-shaped configuration as a consequence of its material characteristics.

37 Claims, 5 Drawing Sheets

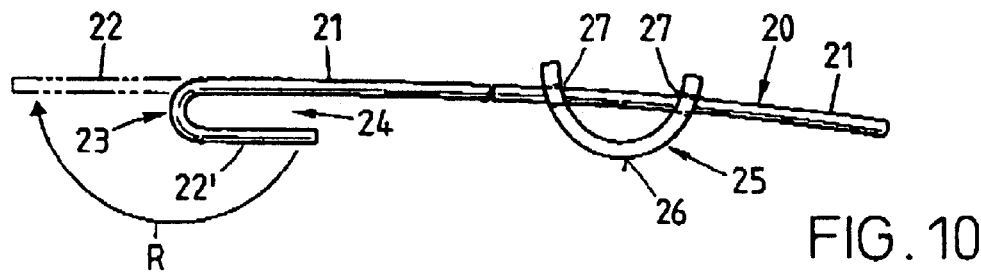
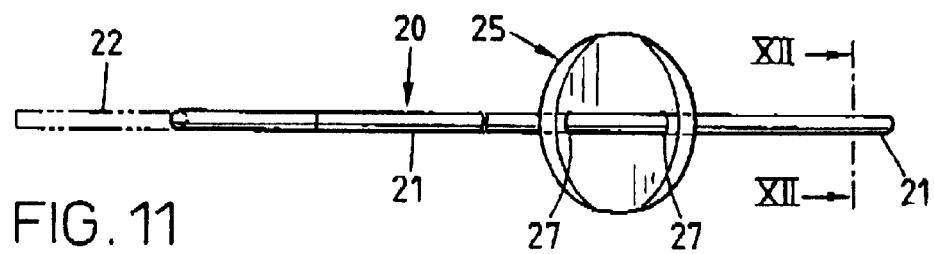
  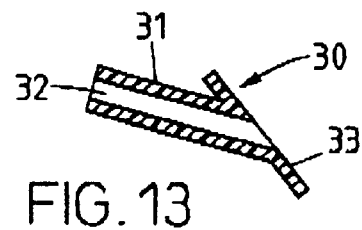
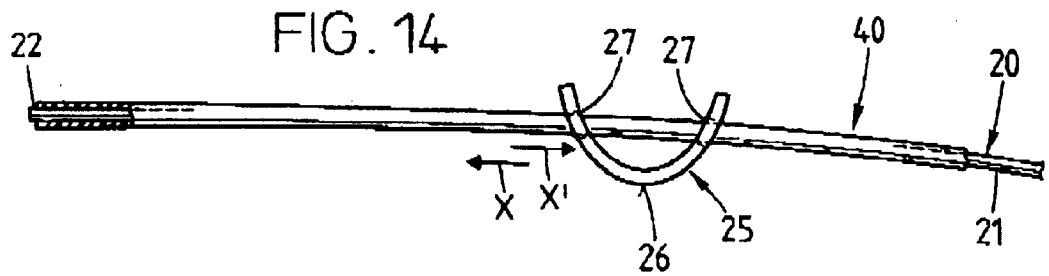
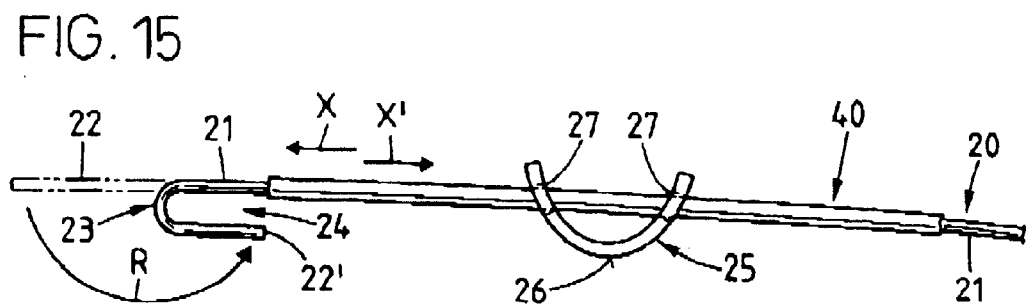

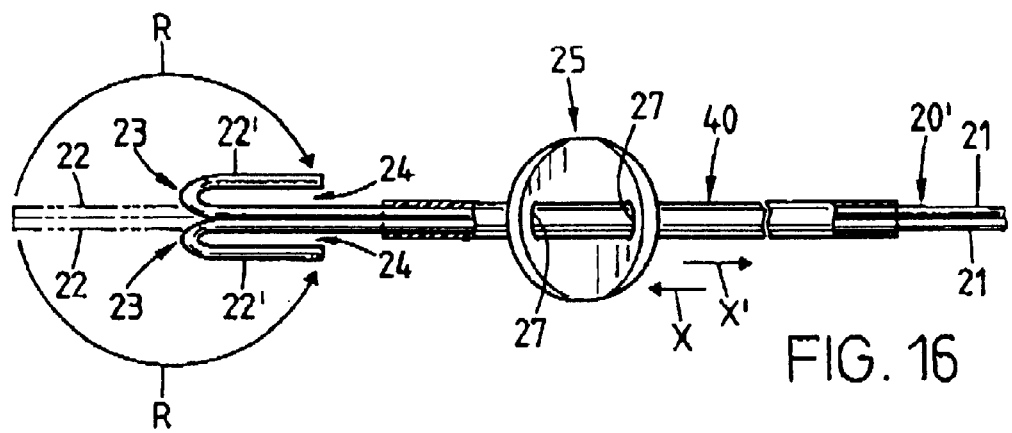
FIG. 16
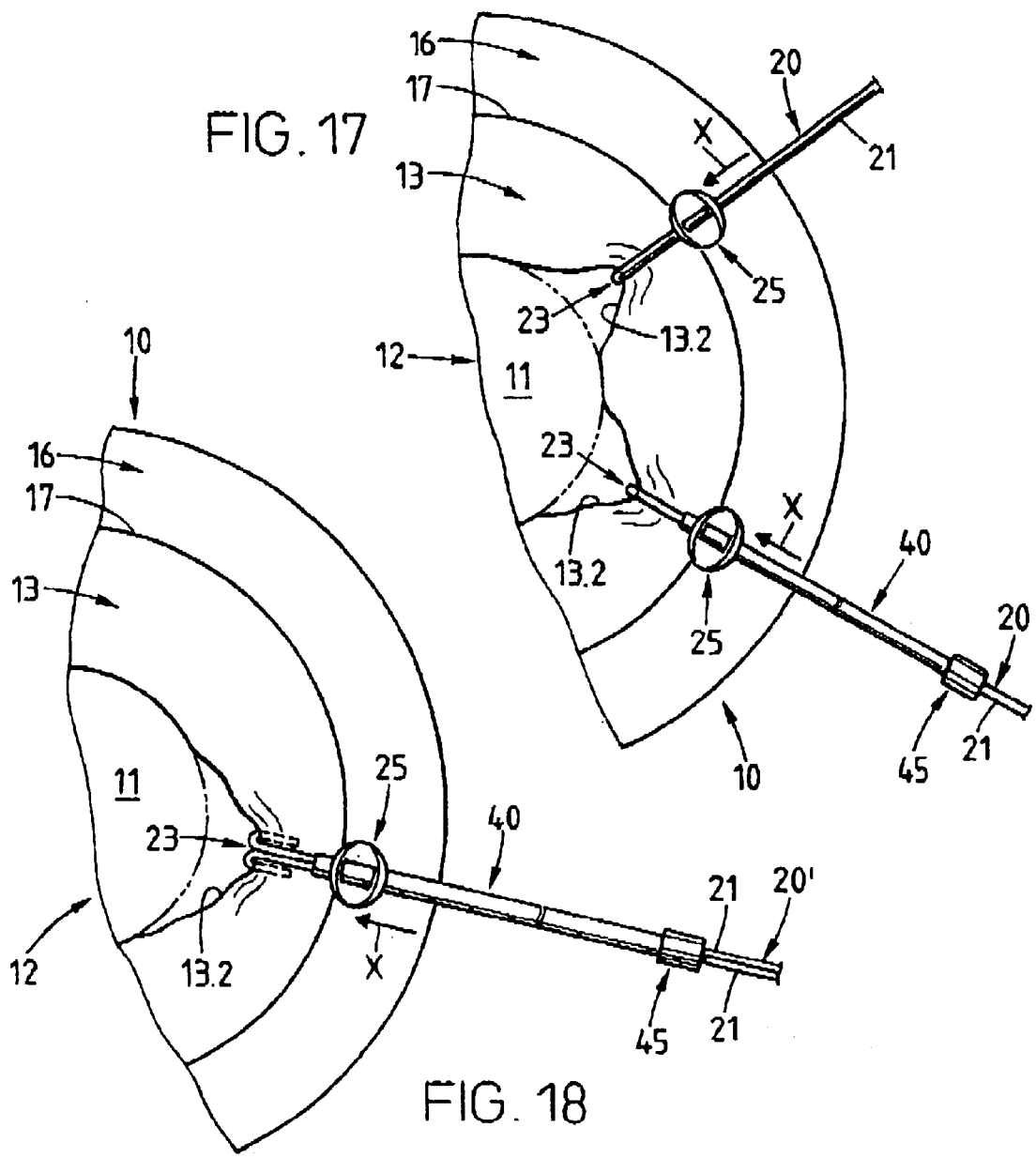
FIG. 17
FIG. 18

DEVICE FOR USE IN A SURGICAL PROCEDURE ON AN EYE OF A LIVING BEING, AND METHOD OF RETRACTING THE IRIS

BACKGROUND OF THE INVENTION

The present invention relates to a surgical device for use in ophthalmic surgery, and in particular to a retraction member for use in eye surgery of a living being for retraction of the iris.

Retraction members typically include an elongated body portion with a substantially hook-shaped end for retracting the iris, and a fixation element slideably mounted on the body portion for securing the retraction member in place when the body portion is inserted with its hook-shaped end into the anterior chamber through a suitable incision made in the cornea.

It is well known that adequate dilatation of the pupil of the eye is essential during e.g. cataract surgery. In particular, for removal of a cataract, the surgical procedure in the posterior section as well as anterior section of the eye requires a sufficiently large and constant viewing range for the surgeon. Generally, the dilatation of the pupil is effected through administration of pharmaceuticals. However, on occasions, the use of pharmaceuticals is insufficient to attain the desired dilatation so that the use of surgical instruments for retracting the iris is proposed, e.g. application of one or more suitably spaced iris retractors which attach to the iris to pull it outwardly for enlarging the opening of the pupil. The individual iris retractors are inserted into the anterior chamber of the eye through an incision in the cornea and suitably fixed in tight manner by the fixation element at the outer contour of the eye. After surgery, the iris retractor is released from the iris and withdrawn from the anterior chamber of the eye.

European Pat. No. 0 653 197 describes an iris retractor for use in the ophthalmic surgery, with the iris retractor having a body portion formed at one end with a hook-shaped engagement part for insertion into the anterior chamber of the eye and withdrawal of the iris. A plate-shaped fixation element is slideably mounted to the body portion to hold the body portion in place in the region of the transition area from the cornea to the sclera. The iris retractor is inserted into the anterior chamber via an incision in the cornea and withdrawn after conclusion of the surgical procedure.

U.S. Pat. No. 5,716,328 describes an iris retractor which includes an elongated body portion of flexible material for insertion through an incision in the eye to retract the iris, with the body portion including two parallel shafts secured to each other along a common longitudinal edge wherein each shaft has at least one end formed with a hook-shaped member. The shafts of the body portion are so joined together that the hook-shaped members diverge from the longitudinal edge downward at an angle to one another to exhibit a Λ-shaped configuration, to thereby cover a widest possible range of the iris.

The use of such iris retractors for ophthalmic surgery in the anterior or posterior eye sections suffers, however, shortcomings insofar as they require an incision which must be sized at least as wide as the entire width of the hook-shaped engagement part to prevent inadvertent, traumatic lacerations.

SUMMARY OF THE INVENTION

It is thus an object of the present invention to provide an improved iris retractor, obviating the afore-stated drawbacks.

In particular, it is an object of the present invention to provide an improved retraction member which requires a comparably much smaller incision in the cornea for insertion into and withdrawal from the anterior chamber, and yet is able to substantially decrease a risk of injury to the eye, in particular during withdrawal of the retraction member.

These objects, and others which will become apparent hereinafter, are attained in accordance with the present invention by providing a retraction member having a hook-shaped engagement part for retracting the iris, with at least the engagement part of the retraction member being made of a deformable material with shape memory so that the retraction member is insertable into the anterior chamber with the engagement part in a substantially straight configuration, and subsequently the engagement part is able to recover its original hook-shaped configuration as a consequence of its material characteristics, to implement a retraction of the iris.

A retraction member according to the present invention requires only a relatively small incision in the cornea for insertion into or withdrawal from the anterior chamber, whereby the incision seals itself once the retraction member is withdrawn.

According to another feature of the present invention, the retraction member may be received in an elongate tube, which is insertable together with the engagement part of the retraction member in straight configuration into the anterior chamber, whereas a relative movement in axial direction between the tube and the retraction member clears the engagement part to allow recovery of its original hook-shaped configuration.

The retraction member may be a filament with shape memory and made over its entire length of flexible, polymeric material e.g. thermoplastic material such as polyamide, or metal, e.g. a nickel-titanium alloy. The engagement part is bendable into the straight configuration for insertion into the anterior chamber at a temperature below a temperature in the anterior chamber and recovers the hook-shaped configuration as a result of the elevated temperature in the anterior chamber. For example, the engagement part of the retraction member can be bent into the substantially straight configuration at a room temperature of about 18° C. to 22° C. for insertion into the anterior chamber, and recovers its original hook-shaped configuration when heated in the anterior chamber to a body temperature of the living being of about 35° C. to 37° C.

According to another feature of the present invention, the filament and/or the tube may be dyed with an optical warning color, preferably a color that contrasts a hue of the iris.

According to another feature of the present invention, a sleeve may be placed in the cornea for insertion of the retraction member, with the sleeve having a tubular member projecting into the anterior chamber and providing an abutment for upward bending of the engagement part when the retraction member is withdrawn.

Suitably, a fixation element is provided which is slideably secured to the retraction member or the tube and clampable in a desired position, whereby the fixation element has a disk-like configuration and is made of a caoutchouc mixture exhibiting an optical warning color.

BRIEF DESCRIPTION OF THE DRAWING

The above and other objects, features and advantages of the present invention will be more readily apparent upon reading the following description of preferred exemplified embodiments of the invention with reference to the accompanying drawing, in which:

FIG. 10 is a side view, on an enlarged scale, of the retraction member of FIG. 1 with slideably attached fixation element;

FIG. 11 is a top view of the retraction member of FIG. 10;

FIG. 12 is cross-sectional view of the retraction member, taken along the line XII—XII in FIG. 11;

FIG. 12A is cross-sectional view of a modified retraction member;

FIG. 13 is a detailed, sectional view, on an enlarged scale, of the sleeve of FIG. 6;

FIG. 14 is a side view, on an enlarged scale, of the combined arrangement of retraction member and tube of FIG. 7;

FIG. 15 is a side view of the arrangement of FIG. 14, with the retraction member partially pushed out from the tube;

FIG. 16 is a top view, on an enlarged scale, of a modified retraction member according to the present invention comprised of two body portions received in a tube;

FIG. 17 is a schematic plan view of a portion of the eye with the iris being retracted by the retraction member of FIG. 10 and the combined arrangement of retraction member and tube according to FIG. 15; and FIG. 18 is a schematic plan view of a portion of the eye with the iris being retracted by the retraction member of FIG. 16.

DETAILED DESCRIPTION OF PREFERRED EMBODIMENTS

Figure 1:
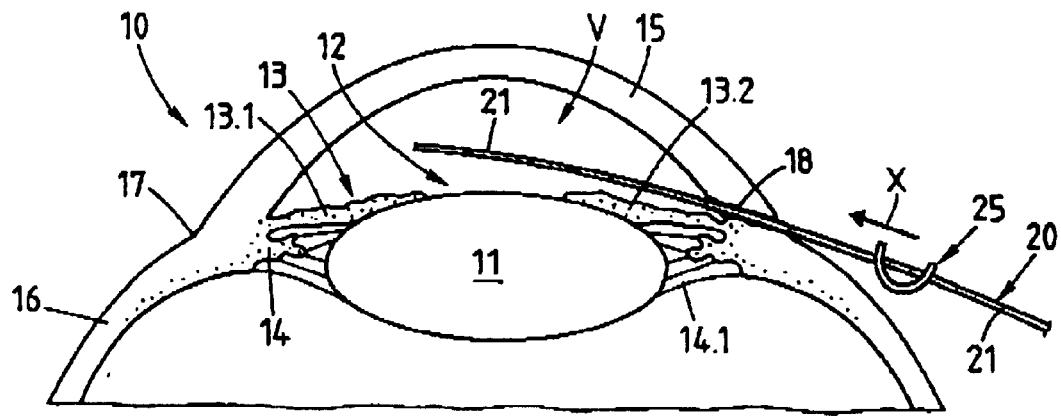
FIG. 1 is a horizontal section, on an enlarged scale, of a portion of an eye, having retraction member according to one embodiment of the present invention inserted in its anterior chamber, with the retraction member having a straight configuration.

Throughout all the Figures, same or corresponding elements are generally indicated by same reference numerals.

Turning now to the drawing, and in particular to FIG. 1, there is shown an enlarged schematic illustration of the forward eye section of a living being, generally designated by reference numeral 10 and including the anterior chamber, designated in its entirety by reference character V, the lens 11 (ocular), the pupil 12, the iris generally designated by reference numeral 13 and including both circular areas 13.1 and 13.2, the zonule fibers 14.1 as well as the ciliary bodies 14, the cornea 15, the sclera 16 and the transition 17 (corneal limbus) from the cornea 15 to the sclera 16. For a surgical procedure in the anterior eye section as well as in the posterior eye section, the provision of a greatest possible and constant viewing field for the surgeon (ophthalmologist) is a prerequisite for a successful procedure. To accomplish a desired viewing field, a retraction member, generally designated by reference numeral 20, is inserted in a direction indicated by arrow X into the anterior chamber V through an incision 18 made by means of a suitable instrument in the area of the transition 17 between the cornea 15 and the sclera 16. The retraction member 20 includes an elongate, flexible body portion 21 and a fixation element 25 which is mounted on the body portion 21 for displacement in longitudinal direction and clampable in a desired position to hold the retraction member 20 in proper position at the transition 17. The fixation element 25 is suitably elastically deformable and provided with an arcuate seat surface 26 (FIG. 10) to substantially conform to the transition 17.

Figure 2:
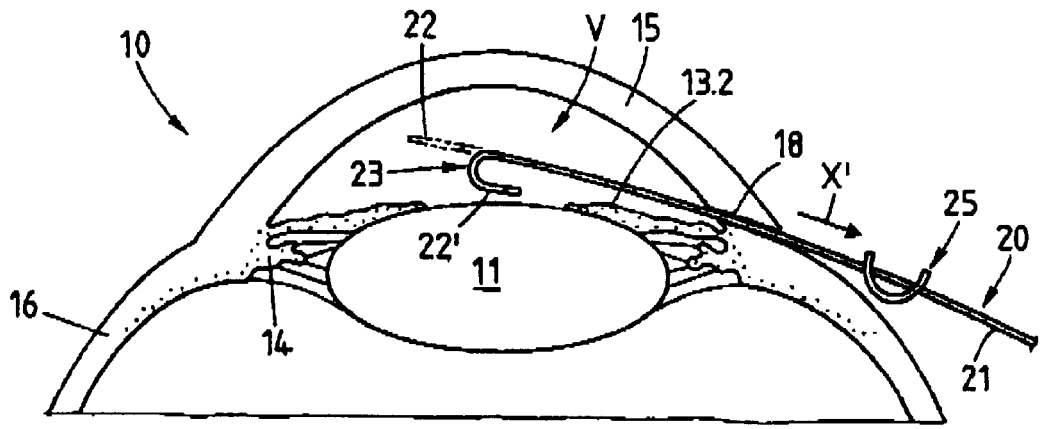
FIG. 2 is a horizontal section, on an enlarged scale, of the portion of the eye, illustrating the retraction member after recovery of its original shape with hook-shaped engagement part for retracting the iris.

The substantially flexible body portion 21 of the retraction member 20 may be made of metal, for example, a nickel-titanium alloy, or of a suitable polymeric material, e.g. thermoplastic material such as polyamide, whereas the fixation element 25 may be made of an elastically deformable material such as a caoutchouc mixture, e.g. a silicone caoutchouc mass. In accordance with the present invention, the material for the body portion 21 is so selected that at least a forward section thereof, that is insertable into the anterior chamber V and designated in FIG. 2 by reference numeral 22, preferably however the entire elongate body portion 21, is deformable and has a shape memory that allows the material after deformation to recover its original shape, for example, when being subjected to the higher temperature that is prevalent in the anterior chamber V (typically of about 35° C. to 37° C.). In its original shape, the forward section 22 of the retraction member 20 has a hook-shaped configuration to define an engagement part 23 (FIG. 2). However, upon insertion through the incision 18 into the anterior chamber V, the forward section 22 of the retraction member 20 is bend upwards to give the retraction member 20 a straight configuration, as shown in FIG. 1, so that the incision 18 can be sized of minimal dimension.

Figure 3:
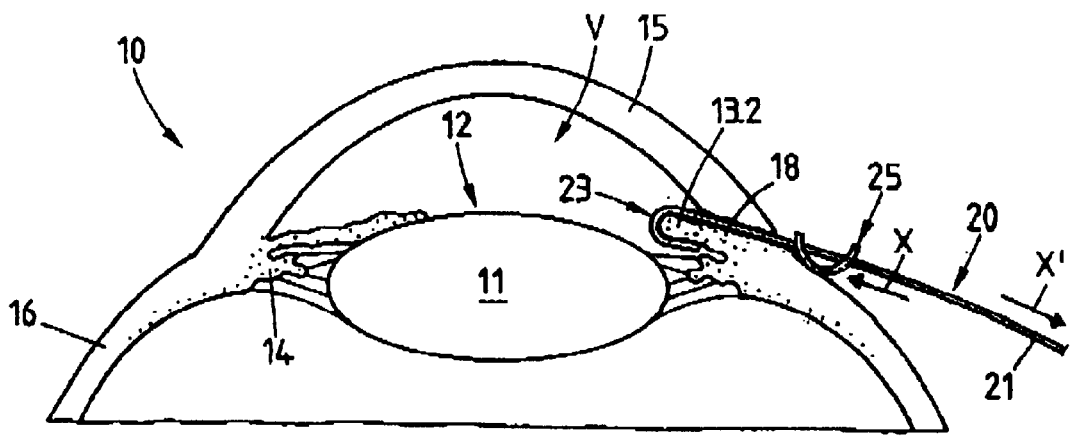
FIG. 3 is a horizontal section, on an enlarged scale, of the portion of the eye, illustrating the retraction member hooked to the iris and held in position by a fixation element near the corneal limbus.

When the retraction member 20 has been inserted into the anterior chamber V, the forward section 22 will recover its original shape, e.g. as a result of the elevated temperature inside the anterior chamber V, to assume the hook-shaped configuration, thereby forming the engagement part 23, as shown in FIG. 2. As soon as the retraction member 20 recovers its original shape and is formed with the engagement part 23, the surgeon moves the body portion 21 for engagement with the respective one of the circular areas (here circular area 13.2) of the iris 13 and draws the retraction member 20 backwards in direction of arrow X' (FIG. 3). The retraction member 20, including the engagement part 23 attached to the circular area 13.2, is thereby secured in place by the fixation element 25. FIG. 3 shows a maximal outer position of the retraction member 20 with the circular area 13.2 of the iris 13, whereby the fixation element 25 is moved in direction of arrow X to bear upon the outer contour of the eye 10 in the area of the transition 17 (corneal limbus) and clamped upon the body portion 21.

Figure 4:
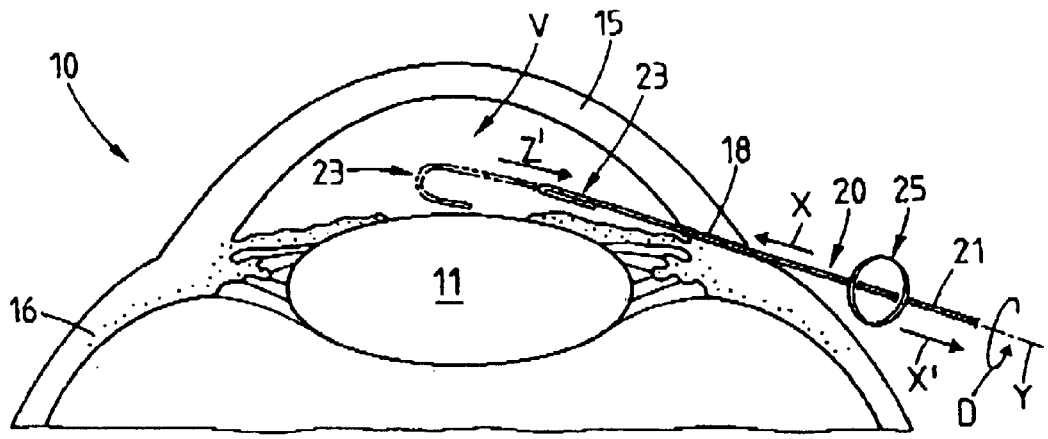
FIG. 4 is a horizontal section, on an enlarged scale, of the portion of the eye, illustrating the retraction member pushed further into the anterior chamber for detachment of the engagement part from the iris.
Figure 5:
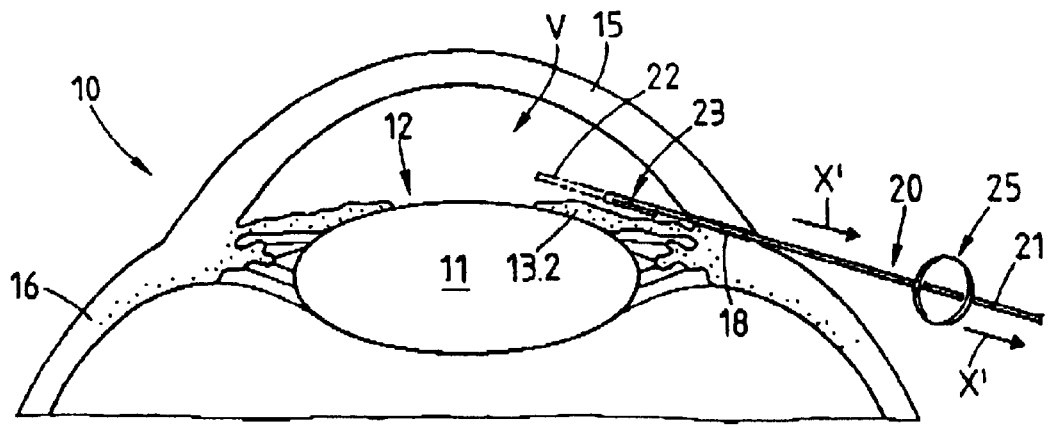
FIG. 5 is a horizontal section, on an enlarged scale, of the portion of the eye, illustrating the retraction member substantially withdrawn from the anterior chamber.

After conclusion of the surgical procedure, the fixation element 25 is released and moved in the direction of arrow X', as shown in FIG. 4. Subsequently, the retraction member 20 is pushed into the anterior chamber V in the direction of arrow X to thereby detach the engagement part 23, as indicatedin broken line from the circular area 13.2 of the iris 13 so that the circular area 13.2 can assume its natural position. Withdrawal of the retraction member 20 from the anterior chamber V is implemented by suitably twisting the elongate body portion 21 of the retraction member 20 in the direction of arrow D at an angle of about 90° about its own longitudinal axis Y, thereby preventing the engagement part 23 from re-attaching to the circular area 13.2, when the retraction member 20 is withdrawn in the direction X', as shown in FIG. 5. As a consequence of its innate elasticity, the engagement part 23 is progressively bent upwards during withdrawal of the retraction member 20 in the direction of arrow X' so that the forward section 22 of the retraction member 20 is ultimately straightened again, as indicated by broken line, for removal of the retraction member 20 from the anterior chamber V.

Figure 6:
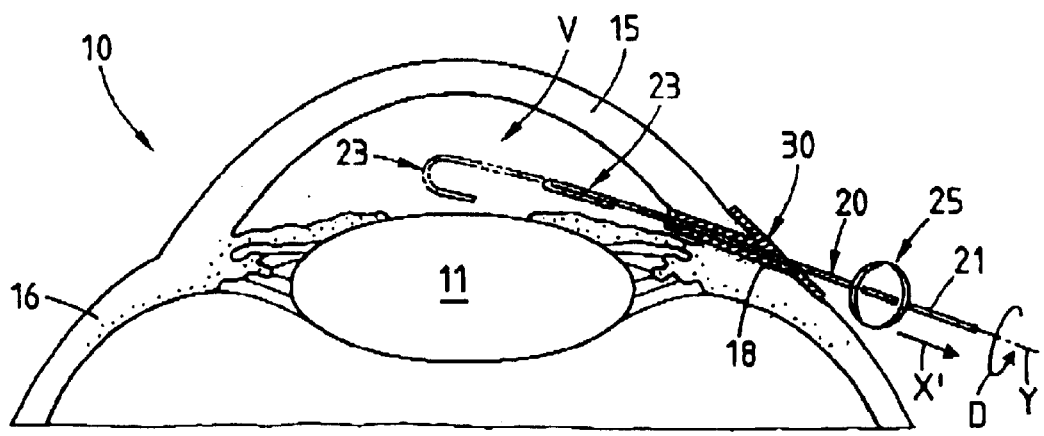
FIG 6 is a horizontal section, on an enlarged scale, of the portion of the eye, illustrating the provision of a sleeve near the corneal limbus for facilitating insertion and withdrawal of the retraction member.

Turning now to FIG. 6, there is shown the placement of a sleeve 30 in the incision 18 in the cornea 15 to ensure a precise insertion of the straightened retraction member 20 in the anterior chamber V and to provide an abutment for straightening the engagement part 23 during withdrawal of the retraction member 20 from the anterior chamber V. In particular during withdrawal of the retraction member 20, the sleeve 30 prevents injury of the inner wall surface of the anterior chamber V by the engagement part 23 which is not yet fully straightened in this phase.

Figure 7:
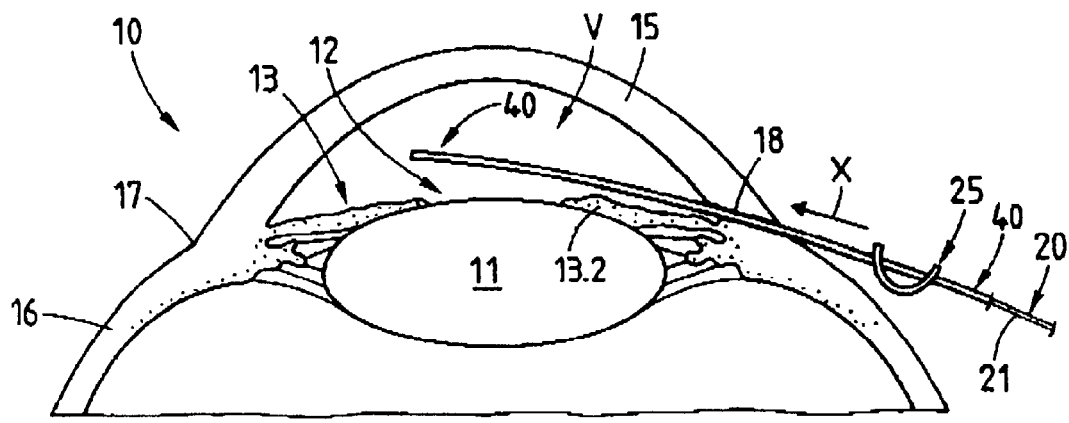
FIG. 7 is a horizontal section, on an enlarged scale, of the portion of an eye, having inserted therein in its anterior chamber a combined arrangement of a retraction member and a tube.

FIG. 7 shows the provision of a probe or tube 40 for facilitating introduction of the retraction member 20 into the anterior chamber V. Prior to the introduction, the body portion 21 of the retraction member 20 is placed coaxially in the tube 40, thereby necessarily straightening the hook-shaped engagement part 23 as the body portion 21 is pushed into the tube 40. With the retraction member 20 received in the tube 40, the tube 40 is inserted through the incision 18 in direction of arrow X into the anterior chamber V of the eye 10. The fixation element 25 is attached to the outer circumference of the tube 40 for displacement in axial direction and can be clamped at any desired position.

Figure 8:
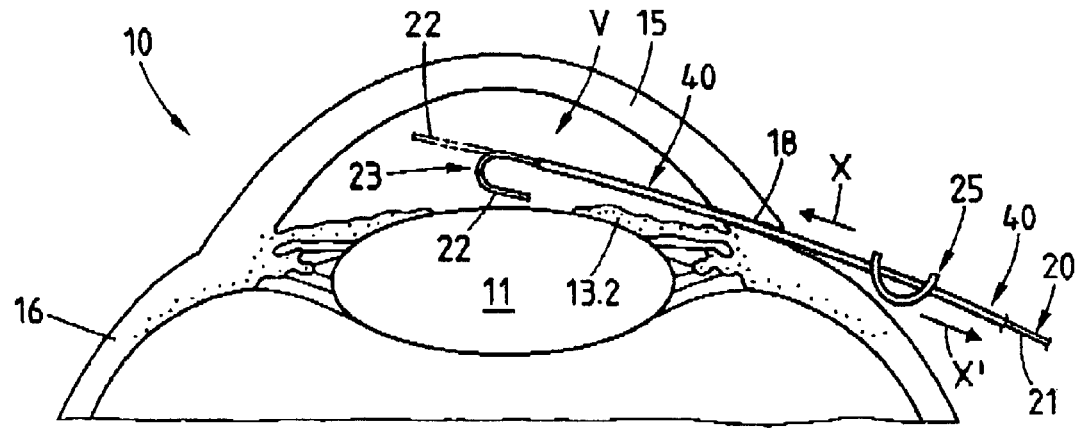
FIG. 8 is a horizontal section, on an enlarged scale, of the portion the eye of FIG. 7, illustrating a relative displacement between the retraction member and the tube to clear a forward end of the retraction member for recovery to its original shape with hook-shaped engagement part for retracting the iris.
Figure 9:
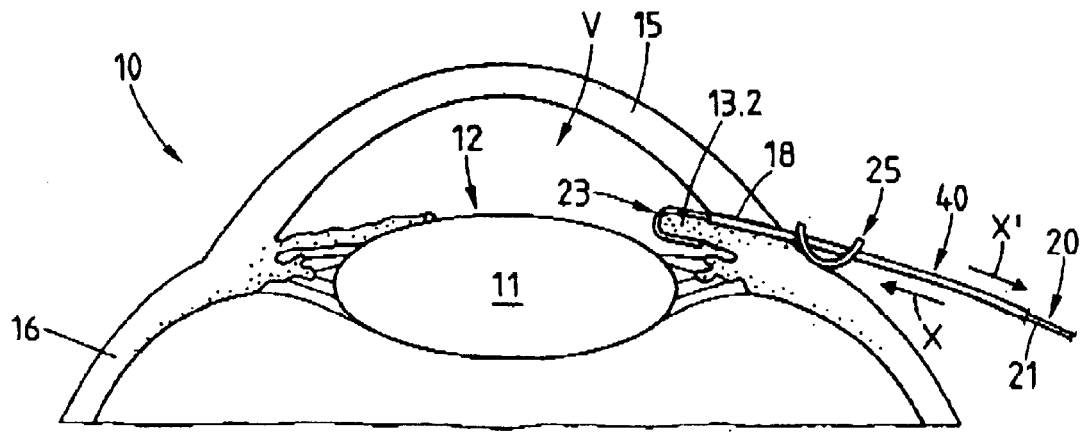
FIG. 9 is a horizontal section, on an enlarged scale, of the portion of the eye of FIG. 7, illustrating the retraction member hooked to the iris with the tube held in position by a fixation element near the corneal limbus.

When the tube 40 with the straight retraction member 20 is inserted in the anterior chamber V, the tube 40 is shifted relative to the retraction member 20 in the direction of arrow X' to thereby clear the forward section 22, shown in broken line, which, as a consequence of its material characteristics, or a period of time etc., or as a consequence of the elevated temperature in the anterior chamber V, recovers its original shape to form the hook-shaped engagement part 23, as indicated in FIG. 8. Subsequently, the retraction member 20 and the tube 40 are pulled back in the direction of arrow X' for attachment of the engagement part 23 to the respective one of the circular areas 13.1, 13.2 of the iris 13 (here circular area 13.2). The fixation element 25 secures the tube 40 and thus the circular area 13.2 via the retraction member 20 in place at any desired position by shifting the fixation element 25 in the direction of arrow X. FIG. 9 shows the maximum outermost position of the tube 40 with accommodated retraction member 20 for the surgical procedure, with the fixation member 25 bearing upon the outer contour of the eye 10 to secure the tube 40 in place. In this position, i.e. when the iris 13 is retracted, the body portion 21 is secured in place, for example by the friction at the inside wall of the tube 40 or, if necessary, by other measures that are known to the artisan, to prevent the circular area 13.2 of the iris 13 from drawing the retraction member 20 back into the anterior chamber V. As shown in FIGS. 17 and 18, it is, of course, also conceivable to provide another fixation element, such as fixation or stopper element 45, near the engagement-part-distal end of the body portion 21 to secure the retraction member 20 in place by resting against the confronting end of the tube 40.

After surgical procedure, the fixation element 25 in the embodiments, shown in FIGS. 7 to 9, is initially withdrawn in the direction of arrow X' and subsequently, the tube 40 is pushed together with the retraction member 20 in the direction of arrow X into the anterior chamber V. As soon as the hook-shaped engagement part 23 is detached from the circular area 13.2, the guide body 21 with the engagement part 23 is pulled inwardly into the tube 40 to thereby bend the engagement part 23 upwards and thus to straighten the retraction member 20. Then, the tube 40 and the retraction member 20 are withdrawn from the anterior chamber V through movement in the direction of arrow X'. As the tube 40 is removed from the anterior chamber V together with the retraction member 20, there is no need to straighten the hook-shaped engagement part 23 in the region of the irido-corneal angle (angulus irido-cornealis).

As the retraction member 20 is made of shape memory material, the incision 18 in the cornea 15 for insertion of the retraction member 20 can be implemented by a suitable surgical instrument, e.g. scalpel or knife or the like, of a width of only about 0.2 mm to 0.4 mm. This comparably small incision 18 can seal itself without additional measures after withdrawal of the retraction member 20. The same is true even when using a tube 40, as shown in FIGS. 7 to 9, when considering that the retraction member 20 has a diameter of 0.15 mm and the suitably thinwall tube 40 has an outer diameter of about 0.25 mm to 0.35 mm.

Turning now to FIG. 10, there is shown a side view, on an enlarged scale, of the retraction member 20 and the fixation element 25 which is slideably attached to the elongate, flexible body portion 21. In the original shape, the forward section 22 is bent over once in a hairpin-like manner to provide the hook-shaped engagement member 23 whereby a shank 22' is formed which extends in parallel relation at a distance 24 to the body portion 21. The fixation member 25 which can be shifted along the body portion 21 may be configured, for example, as a circular disk (cf. FIG. 11) having two spaced-apart bores 27 for passage of the body portion 21. The bores 27 are so arranged relative to one another that the flexible fixation member 25 can be shifted along the body portion 21, when squeezed together, and is held in place at a desired location, when releasing the fixation member 25, whereby the arcuate seat surface 26, formed by the fixation member 25, rests on the outer contour of the eye 10 in the area of the corneal limbus. As shown in FIG. 12, the body portion 21 may have a circular cross section, or, as shown in FIG. 12A, an elliptic cross section.

The flexible body portion 21 of the retraction member 20 is designed in the form of a filament or thread whereby at least the hook-shaped engagement part 23 is made of deformable material with shape memory. Of course, it is also possible to produce the retraction member 20 in its entirety of a deformable material with shape memory. Examples of suitable materials for the body portion 21 include a shape memory metal alloy, e.g. nickel-titanium alloy, with a so-called "super-elasticity", or polymeric material such as thermoplastic material, e.g. polyamide.

Prior to introduction of the retraction member 20 into the anterior chamber V of the eye 10, the shank 22' of the engagement part 23 is bent upwards in the direction of arrow R, as indicated in FIG. 10, to straighten the body portion 21, as shown in broken line, at a temperature that is below the temperature in the anterior chamber V, for example at a room temperature between 18° C. and 22° C., for example of about 20° C. In straight configuration, the retraction member 20 is inserted into the anterior chamber V of the eye 10 through the incision 18. Subsequently, as a consequence of the particular material properties and the elevated temperature in the anterior chamber V of the eye 10 of about 35° C. to 37° C., the forward section 22 of the retraction member 20 reverts by itself to its original shape, i.e. to form the hook-shaped engagement part 23, with the shank 22' spaced at the distance 24 in parallel relationship from the body portion 21.

Referring now to FIG. 13, there is shown a detailed sectional view of the sleeve 30 being disposed in the incision 18, as shown in FIG. 6. The sleeve 30 includes a tubular member 31 having a throughbore 32 and one end formed integrally with a flange 33 which extends at an angle to the throughbore 32 to ensure a sealing contact of the sleeve 30 upon the cornea 15 (cf. FIG. 6).

FIG. 14 is a detailed illustration of the elongate tube 40 for receiving the retraction member 20, with the fixation element 25 slideably mounted on the tube 40 in direction of arrows X, X' and clampable at any desired position on the tube 40. The retraction member 20 and the fixation element 25 are constructed in a manner described above with reference to FIGS. 10 and 11. The body portion 21 of the retraction member 20 is received in the tube 40 so that the forward section 22 is straight, ensuring insertion of the tube 40 into the anterior chamber V of the eye 10 through the incision 18 without any problems, as depicted in FIG. 7. A relative movement between the retraction member 20 and the tube 40, by either pushing the retraction member 20 relative to the tube 40 in the direction of arrow X, or by pulling the tube 40 relative to the retraction member 20 in the direction of arrow X', clears the forward section 22 which, as a consequence of the shape memory, recovers its original hook-shaped configuration to form the engagement part 23 by moving in the direction-of arrow, as depicted in FIG. 15. In this position, the shank 22' extends in approximate parallel disposition to the body portion 21 at the distance 24. Persons skilled in the art will understand that the body portion 21 may be provided at its engagement part distal end with a grip for better handling of a relative movement between the retraction member 20 and the tube 40.

In accordance with a modified embodiment, shown in FIG. 16, the tube 40 accommodates a modified retraction member 20' with two adjoining body portions 21 in the form of filaments and in coextensive parallel disposition. Also in this embodiment, either the retraction member 20' with both body portions 21 is pushed relative to the tube 40 in the direction of arrow X, or the tube 40 is pulled relative to the retraction member 20' in the direction of arrow X', to clear the forward section 22 of each body portion 21. As a consequence of the shape memory, the straight forward sections 22, shown in broken lines, are caused to bend into the hook-shaped configuration to form the engagement parts 23, with the shanks 22' extending parallel to the body portions 21 and arranged at an acute angle to one another to exhibit a downwardly diverging substantially Λ-shaped configuration. Before insertion of the tube 40 into the anterior chamber V of the eye 10, the retraction member 20' with its two body portions 21 is pulled into the tube 40 to assume the straight configuration.

Referring now to FIG. 17, there is shown a schematic plan view of a portion of the eye 10 with the iris 13 being retracted by a retraction member 20 according to FIG. 10, with the fixation element 25, which is slideably mounted on the retraction member 20, bearing upon the outer contour of the eye 10 at the transition 17 to secure the retraction member 20 in place. Positioned at a distance to the retraction member 20 is a tube 40 according to FIG. 14, which has received therein a retraction member 20 with cleared engagement part 23 for retraction of the iris 13 at another location, whereby the fixation element 25, which is slideably mounted on the tube 40, bears upon the outer contour of the eye 10 at the transition 17 to secure the tube 40 in place. The body portion 21 of the retraction member 20 is held in place, for example, through friction against the inner wall surface of the tube 40 or by the fixation element 45 to prevent a pullback of the retraction member 20 into the anterior chamber V by the iris 13.

In FIG. 18, the retraction member 20' of FIG. 16 with two body portions 21 is used for retraction of the iris 13 and received in a tube 40 having mounted thereon the fixation element 25. The retraction member 20' is pushed out of the tube 40 and attached to the iris 13 via its engagement parts 23. The fixation element 25 bears upon the outer contour of the eye 10 at transition 17 to secure the tube 40 in place. The body portion 21 of the retraction member 20' is held in place through friction against the inner wall surface of the tube 40 or by the fixation element 45.

The body portion 21 of the retraction member 20, 20' is made in the form of a flexible filament or thread and has a diameter of about 0.12 mm to 0.20 mm. Suitably, the body portion 21 is made, at least from an area extending axially from the hook-shaped engagement part 23 to half the entire length of the body portion 21, preferably however over the entire length of the body portion 21, of a shape memory material which has a hue that clearly contrasts the hue of the iris 13 at hand, preferably of a material exhibiting an optical warning color. The body portion 21 may have a circular or elliptic cross section and is advantageously dyed in a homogenous color that contrasts the hue of the iris 13. Persons skilled in the art will understand that at least those portions of the body portion 21 and/or the portion of the tube 40, which are positioned during surgical procedure above the iris 13 should also have a hue which contrasts the hue of the iris 13. Of course, it is certainly conceivable to color, in addition to the retraction member 20, 20', also the tube 40 with a homogenous hue to contrast the hue of the iris 13. Also the fixation member 25 and the fixation element 45 may suitably be made of a caoutchouc mixture, e.g. silicone caoutchouc mass, exhibiting a glaring and visually distinct color.

While the invention has been illustrated and described as embodied in a device for use in a surgical procedure on an eye of a living being, and method for retracting the iris, it is not intended to be limited to the details shown since various modifications and structural changes may be made without departing in any way from the spirit of the present invention.

What is claimed as new and desired to be protected by letters patent is set forth in the appended claims:

What is claimed is:

1. A device for use in a surgical procedure on an eye of a living being, comprising a retraction member, destined for insertion into the anterior chamber of the eye, said retraction member made of a flexible filament and having a hook-shaped engagement part for retracting the iris, at least said engagement part of the retraction member being made of a deformable material with shape memory so that the retraction member is insertable into the anterior chamber with the engagement part in a substantially straight configuration, and subsequently the engagement part is able to recover its original hook-shaped configuration as a consequence of its material characteristics, to implement a retraction of the iris, wherein the engagement part of the retraction member is bendable into the straight configuration for insertion into the anterior chamber at a temperature below a temperature in the anterior chamber and recovers the hook-shaped configuration as a result of the temperature in the anterior chamber.

2. The device of claim 1, and further comprising an elongate tube insertable into the anterior chamber, said retraction member being so received in the tube that the engagement part has a straight configuration, wherein a relative movement in axial direction between the tube and the retraction member clears the engagement part to permit subsequent recovery of its hook-shaped configuration.

3. The device of claim 2 wherein the retraction member is a flexible filament made over its entire length of a metal with mechanical shape memory based on inherent elasticity.

4. The device of claim 3 wherein the metal is a nickel-titanium alloy.

5. The device of claim 2 wherein the tube and the retraction member have each a forward section insertable into the anterior chamber, at least said forward section of said tube and said retraction member being made of a material which is dyed with a warning color.

6. The device of claim 2 wherein the material has a homogenous hue which contrasts the hue of the iris.

7. The device of claim 2 wherein the tube and the retraction member are made over their entire length of a material having an optical warning color.

8. The device of claim 2, and further comprising a first fixation element slideable and clampable on the tube and a second fixation element slideable and clampable on the retraction member for securing the retraction member in position when the engagement part hooks onto the iris.

9. The device of claim 8 wherein the first and second fixation elements are made of a caoutchouc mixture exhibiting an optical warning color.

10. The device of claim 1, and further comprising an elongate tube, said retraction member having at least two such engagement parts and so received in the tube that the engagement parts have a straight configuration, wherein a relative movement in axial direction between the tube and the retraction member clears the engagement parts to permit subsequent recovery of their hook-shaped configuration, whereby the engagement parts diverge at an angle to one another to exhibit a Λ-shaped configuration.

11. The device of claim 10 wherein the retraction member is a flexible filament made over its entire length of a metal with mechanical shape memory based on inherent elasticity.

12. The device of claim 11 wherein the metal is a nickel-titanium alloy.

13. The device of claim 10 wherein the tube and the retraction member have each a forward section insertable into the anterior chamber, at least said forward section of said tube and said retraction member being made of a material which is dyed with a warning color.

14. The device of claim 13 wherein the material has a homogenous hue which contrasts the hue of the iris.

15. The device of claim 10 wherein the tube and the retraction member are made over their entire length of a material having an optical warning color.

16. The device of claim 10, and further comprising a first fixation element slideable and clampable on the tube and a second fixation element slideable and clampable on the retraction member for securing the retraction member in position when the engagement part hooks onto the iris.

17. The device of claim 16 wherein the first and second fixation elements are made of a caoutchouc mixture exhibiting an optical warning color.

18. The device of claim 1 wherein at least the engagement part of the retraction member is made of a flexible, polymeric material with thermal shape memory.

19. The device of claim 18 wherein the engagement part of the retraction member is capable of recovering the hook-shaped configuration as a consequence of its inherent elasticity and thermal shape memory.

20. The device of claim 1 wherein the retraction member is a flexible filament made over its entire length of a flexible polymeric material with thermal shape memory.

21. The device of claim 20 wherein the flexible filament is made of thermoplastic material.

22. The device of claim 1 wherein at least the engagement part of the retraction member is made of a flexible metal with thermal shape memory.

23. The device of claim 22 wherein the metal is a nickel-titanium alloy.

24. The device of claim 1 wherein the retraction member is a flexible filament made over its entire length of a metal with thermal shape memory.

25. The device of claim 24 wherein the metal is a nickel-titanium alloy.

26. The device of claim 1 wherein the engagement part room is bendable into the straight configuration at a room temperature of about 18° C. to 22° C. and recovers the hook-shaped configuration when heated in the anterior chamber to a body temperature of the living being of about 35° C. to 37° C.

27. The device of claim 1 wherein the retraction member is a flexible filament dyed with an optical warning color from the engagement part at least in an area destined for placement above the iris.

28. The device of claim 1 wherein the retraction member is a flexible filament dyed over its entire length with an optical warning color.

29. The device of claim 1 wherein the retraction member is a flexible filament dyed with a homogenous hue which contrasts a hue of the iris.

30. The device of claim 1, and further comprising a sleeve destined for placement in the cornea for insertion of the retraction member, said sleeve having a tubular member projecting into the anterior chamber and providing an abutment for upward bending of the engagement part when the retraction member is withdrawn.

31. A device for use in a surgical procedure on an eye of a living being, comprising:
 a retraction member, destined for insertion into the anterior chamber of the eye, said retraction member having a hook-shaped engagement part for retracting the iris, at least said engagement part of the retraction member being made of a deformable material with shape memory so that the retraction member is insertable into the anterior chamber with the engagement part in a substantially straight configuration, and subsequently the engagement part is able to recover its original hook-shaped configuration as a consequence of its material characteristics, to implement a retraction of the iris, wherein the engagement part of the retraction member is bendable into the straight configuration for insertion into the anterior chamber at a temperature below a temperature in the anterior chamber and recovers the hook-shaped configuration as a result of the temperature in the anterior chamber; and a fixation element slideable and clampable on the retraction member for securing the retraction member in position when the engagement part hooks onto the iris, said fixation element having a disk-like configuration and is made of a caoutchouc mixture exhibiting an optical warning color.

32. A method of retracting the iris of an eye of a living being for a surgical procedure, comprising the steps of:

inserting a retraction member made of shape memory material in a substantially straight configuration through an incision in the cornea into the anterior chamber to permit a forward section of the retraction member to recover an original hooked end configuration, thereby forming an engagement part; and attaching the engagement part to the iris.

33. A method of retracting the iris of an eye of a living being for a surgical procedure, comprising the steps of:

placing a retraction member made of shape memory material in a tube so that its hooked end is bent upwards into a forward section of straight configuration;

inserting the tube with contained retraction member through an incision in the cornea into the anterior chamber of the eye;

executing a relative movement between the retraction member and the tube to project the forward section beyond the tube to thereby permit the forward section of the retraction member to recover its original hooked end configuration; and attaching the hooked end of the retraction member to the iris.

34. The method of claim 33 wherein the recovery of the forward section to its hooked end configuration is realized as a consequence of innate elasticity.

35. The method of claim 33 wherein the recovery of the forward section to its hooked end configuration is realized through exposure to a temperature which is elevated compared to an ambient room temperature.

36. The method of claim 35 wherein the recovery of its hooked end configuration is realized at a temperature of about 35° C. to 37° C.

37. An iris retractor, comprising a body portion made of a flexible filament and having an end section, at least the end section being made of a deformable material with shape memory so as to assume a hook-shaped configuration, when the end portion of the body portion is inserted into the anterior chamber of an eye, in response to a temperature prevailing in the anterior chamber.

* * * * *